Figure 1:
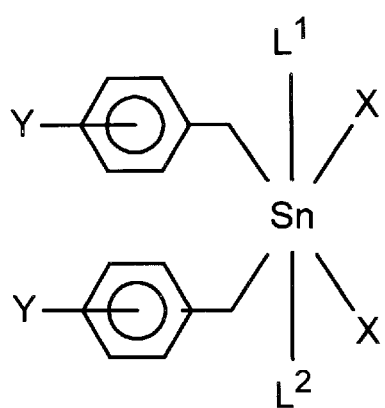
Figure 2:
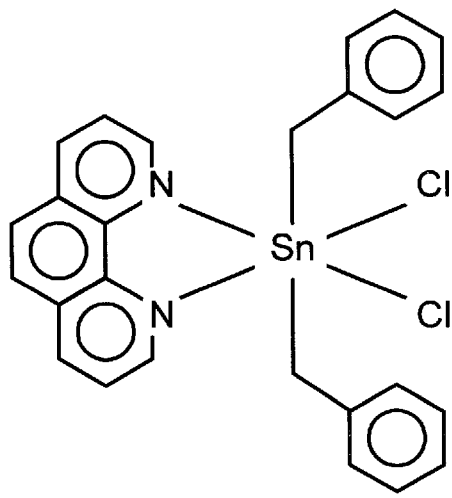
Figure 3:
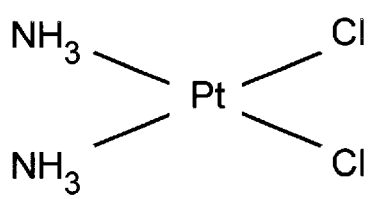
Figure 4:
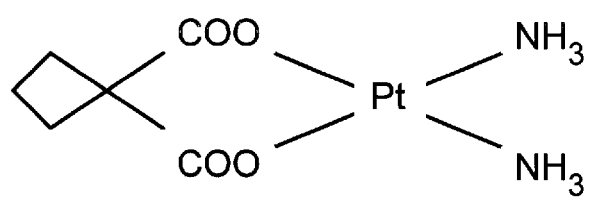
Figure 5:
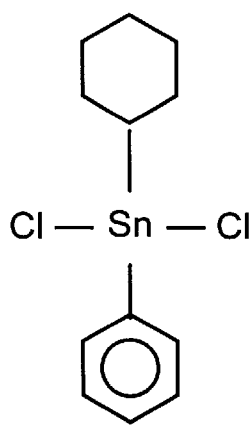
Figure 6:
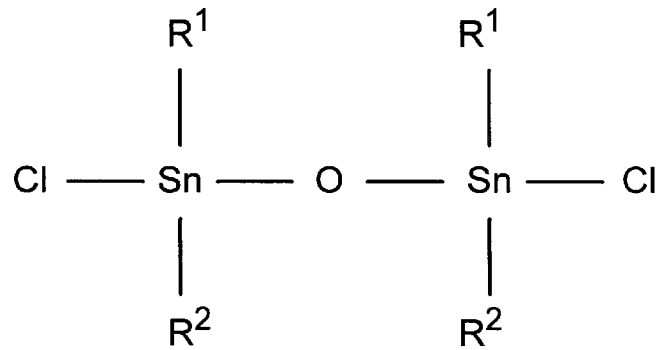

United States Patent
Roy et al.

[11] Patent Number: 5,877,320
[45] Date of Patent: Mar. 2, 1999

[54] PROCESS FOR THE PREPARATION OF ORGANOTIN COMPOUNDS USEFUL AS CYTOTOXIC AGENTS

[75] Inventors: Sujit Roy; Purnima M. Samuel; Prakash V. Diwan; P. Kanta Rao; Uday T. Bhalerao, all of Andhra Pradesh, India

[73] Assignee: Council of Scientific and Industrial Research, New Delhi, India

[21] Appl. No.: 774,029

[22] Filed: Dec. 27, 1996

[30] Foreign Application Priority Data

Dec. 29, 1995 [IN] India ............... 2462/DEL/95

[51] Int. Cl.$^6$ ....................... C07F 7/22
[52] U.S. Cl. ............... 546/6; 549/3; 548/106; 548/108
[58] Field of Search ............... 546/10; 548/106, 548/108; 549/3

[56] References Cited

PUBLICATIONS

Farhangi et al.,Journal of Organometalic Chemistry,vol. 317,pp. 153–157 (1986).
Sisido et al.,Journal of the American Chemical Society,vol. 83,(3),pp. 538–541 Feb. 5, 1961.

*Primary Examiner*—Alan L. Rotman
*Attorney, Agent, or Firm*—Ladas & Parry

[57] ABSTRACT

The present invention is drawn to complexes of dibenzyl-organotin compounds having nitrogen or sulfur containing heterocyclic ligands. Said complexes are useful as cytotoxic agents.

4 Claims, 2 Drawing Sheets

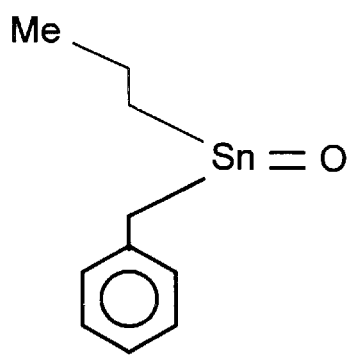
F I G. 7
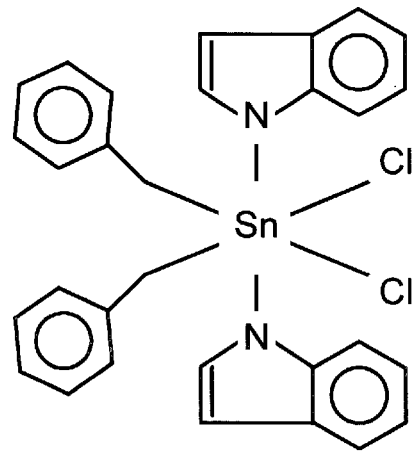
F I G. 8
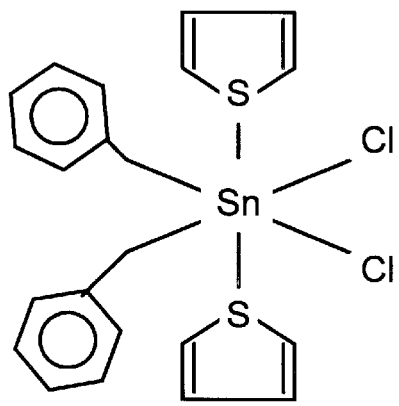
F I G. 9
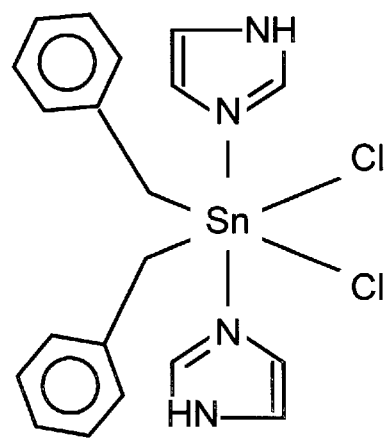
F I G. 10
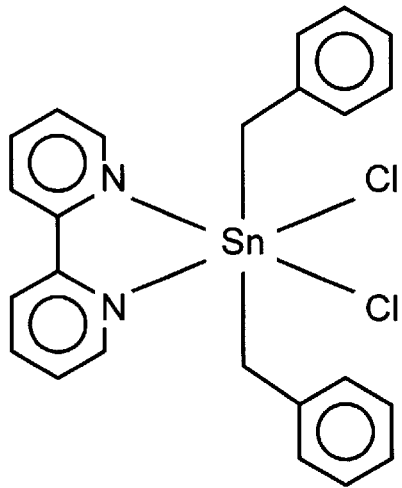
F I G. 11

PROCESS FOR THE PREPARATION OF ORGANOTIN COMPOUNDS USEFUL AS CYTOTOXIC AGENTS

This invention relates to a process for the preparation of organotin compounds useful as cytotoxic agents.

The invention particularly relates to a process for the preparation of compounds of the formula 1 shown in the drawing accompanying this specification where Y represents hydrogen, substituted or unsubstituted alkyl, alkoxy and halo groups; X represents a halogen atom or isothiocyanate group and $L^1$ & $L^2$ represent a monodentate or bidentate ligand with heteroatom such as sulfur, oxygen and nitrogen. The compounds of the formula 1, prepared according to the process of this invention are novel compounds. However, dibenzyl(phenanthroline)-tindichloride of the formula 2, which falls under the general formula 1, has been reported by A. J. Crowe et al. [A. J. Crowe, P. J. Smith & G. Atassi, *Inorg. Chim. Acta,* 93, pp. 179–184 (1984)] and was shown inactive against P388 in mice.

Following the path-breaking success of cis-platin of the formula 3 and carboplain of the formula 4 as effective anticancer drugs, attempts have been made to design other transition and non-transition metal complexes as potential cytotoxic agents. The objective of the investigations being carried out in the area have been to accentuate the tumour inhibition activity vis-a-vis reduce the mammalian toxicity of the new complexes with respect to the platinum drugs. While the above target is yet unaccomplished, many distinct features have emerged from these studies. These features are summarized below in respect of tin compounds.

Diorganotindihalide complexes of the formula $R_2SnX_2.L_2$, where R respresents methyl, ethyl, propyl, butyl & phenyl groups; X reprensents a halogen atom and L represents a bidendate ligand having nitrogen and oxygen donor atom were shown to display significant anti-tumour activity only against P388 lymphocytic leukemia in mice [A. J. Crowe & P. J . Smith, *Chem. Ind.,* pp. 200–201 (1980); A. J. Crowe, P. J. Smith & G. Atassi, *Chem. -Biol. Interact.,* 32, pp 171–178 (1980); N. F. Cardarelli, B. M. Libby & E. P. Dobbins, *Aust. J. Expt. Biol. Med. Sc.,* 62, pp. 209–214 (19.84); W. Jiazhu & J. Huang, *Inorg. Chim. Acta,* 152, pp. 67–69 (1988); H. Shenazhi, S. Dashuang & H. T. Wan, *Inorg. Chim. Acta,* 173, pp. 1–4 (1990)].

A U.S. Pat. No. 4,547,320 [E. J. Bulten & H. A. Budding, assignor to Nederlandse Centrale Organistie, filed Sep. 13, 1982] described the inhibition of P-388 in mice using cyclohexyl-(phenyl)tindichloride of formula 5 and a process for the preparation of the same. The said patent also described the preparation of the compounds having the general formula 6, where $R^1/R^2$ is an alkyl or aryl group and a specific compound of the formula 7 and their anticancer activities.

The above studies have further revealed that a) diethyl and/or diphenyl tin complexes possess the highest activities; b) there is no real link between the Lewis acidity of the parent organotin halide and the P-388 inhibition activity; c) the mode of DNA-binding for these complexes must have a different and yet unknown mechanism than that of cis-platin; d) a pre-dissociation of the bidentate ligand may be the rate limiting step in-vivo and e) the majority of the complexes which show good to excellent activity against P388 in mice are either inactive or poorly active against human cancer cells [A. J. Crowe, P. J. Smith, C. J. Cardin, H. E. Parge & F. E. Smith, *Cancer Lett.,* 24, pp 45–48 (1984); A. J. Crowe, P. J. Smith & G. Atassi, *Inorg. Chim. Acta,* 93, pp 179–184 (1984)]. Dibenzyl(phenanthroline)tindichloride of the formula 2, was shown even to be inactive against P388 in mice [A. J. Crowe, P. J. Smith & G. Atassi, *Inorg. Chim. Acta,* 93, pp 179–184 (1984)]. Further attempts to modify the organogroup by using substituted phenyl tin derivatives [B. N. Biddle & G. Johns, *Appl. Organomet. Chem.,* 3, pp 537–543 (1989)] and alkoxycarbonylmethyltin derivatives [Zhang, Zhenaauan, Pan & Huad et al., *Appl . Organomet. Chem.,* 5, pp. 183–190 (1991)] did not yield to betterment of cytotoxic activity.

Several other tin complexes having diverse structural features, but hot belonging to the structural class of the present invention, have shown either in-vitro or in-vivo cytoxic activities and are described in the following patents: JP 5110089, EP 538517, EP 484596 and EP 472783.

In short, a structure vs. tumour inhibitory activity relationship in organotin compounds is yet to emerge.

The main object of the present invention, therefore, is to provide a process for the preparation of a novel group of tin compounds generally described as dibenzyltin(IV)dihalides/pseudohalides and its complexes with mono or bidentate ligands having heteroatom donor. Another objective of the present invention is to provide a process for the preparation of novel dibenzyltin(IV)dihalides/pseudohalides and their complexes having excellent in-vitro cytotoxicity against human cancer cell lines.

The compounds prepared by the process of the present invention have the general formula 1 where, Y represents hydrogen, substituted or unsubstituted alkyl, alkoxy and halo groups; X represents a halogen atom or thiocyanate, isothiocyanate or isocyanate group and $L^1/L^2$ represent a mondentate/bidentate ligand with heteroatom donor such as sulfur, oxygen or nitrogen. Dibenzyltin(phenanthroline) dichloride of the formula 2 reported earlier by A. J. Crowe, P. J. Smith & G. Atassi [*Inorg. Chim, Acta,* 93, pp 179–184 (1984)] has been excluded from the scope of the present invention.

The aforementioned compounds are synthesized via a multistep procedure the first step being reminiscent of the Rochow process [*J. Am. Chem. Soc.,* 83, pp. 538–541 (1961)]. In the first step tin metal powder and benzyl halide were refluxed in non-halo and non-polar solvents, to afford dibenzyltin dihalide. Dibenzyltin dihalide was treated with alkali metal thiocyanate in non-halo solvents to obtain dibenzyltin diisothiocyanate. Dibenzyltin dihalide/pseudohalide so synthesized was further treated with appropriate ligand in non-polar and non-halo solvents at a temperature in the range of 25°–60° C. to give the desired oganotin compounds of the general formula 1 as defined above.

Accordingly, the present invention provides a process for the preparation of organotin compounds useful as cytotoxic agents of the formula 1 shown in the drawing accompanying this specification where Y represents hydrogen, substituted or unsubstituted alkyl, alkoxy and halo groups; X represents a halogen atom or isothiocyanate group and $L^1$ & $L^2$ halides in the presence of a non-polar and non-halo solvent to yield dibenzyltin dihalide;

by treating 4-desired, the dibenzyltin dihalide with alkali metal thiocyanate, isothiocyanate or isocyanate to produce the corresponding dibenzyltin diisothiocyanate, dithiocyanate, or diisocyanate and finally treating either dibenzyltin dihalide or dibenzyltin dipseudohalide with appropriate ligand in the same solvent at a temperature the range of 25°–60° C. and separating the appropriate compound of the formula 1 by conventional methods.

The tin metal can be used in the form of powder or turnings, preference being the powder of mesh size 100 to 250. The solvents may be toluene, xylene, decaline or a mixture of toluene-decaline in 1:1 ratio. The benzyl halides used may be substituted for benzyl chlorides or benzyl bromides. The amount of tin metal and benzyl halides used may be in the ratio ranging from 1.1:1 to 3:1, preferably in the range of 1.5:1 to 2.1:1. Dibenzyltin dipseudohalide may be substituted for dibenzyltin diisothiocyanate, alkali metal thiocyanate, isothiocyanate or isocyanate may be substituted for sodium or potassium thiocyanate, the non-halo solvent in that step may be any alcohol or acetone. The ligand employed may be substituted for nitrogen containing heterocyles such as imidazole, indole, bipyridine and the like or sulfur containing herterocycles such as thiophene, benzothiophene and the like or oxygen containing heterocycles such as furan, pyran and the like or mixed heterocycles such as thiazole, oxazole and the like.

The in-vitro cytotoxicity determined in terms of inhibition dose [$ID_{50}$] of compounds having the formulae 8–11 prepared by the process of the present invention against eight different human cancer cell lines namely MCF7, EVSAT (Breast Cancer), WIDR (Colon Cancer), IGROV (Ovarian Cancer), M19MEL (Melanoma), A498 (Renal Cancer) and H226 (Nonsmall cell lung Cancer) have been measured following NCI-USA protocol [M. R. Boyd, "Status of the NCI preclinical antitumour drug discovery screen. Principles & practice of oncology 3, pp. 1–12 (1989)] alongwith the latest $ID_{50}$ values of inorganic cancer drugs are presented in Table 1.

TABLE 1

Anti-tumour activity [$ID_{50}$, ng/ml] of tin compounds [Formulae No. 8–11] against Human Cancer cell lines

| CELL LINE | compd. 8 | compd. 9 | compd. 10 | compd. 11 | cis-platin | Carbo-platin |
|---|---|---|---|---|---|---|
| MCF7 | 150 | 68 | 700 | 120 | 1400 | 10500 |
| EVSAT | 150 | 130 | 400 | 150 | 920 | 4500 |
| WIDR | 850 | 550 | 3200 | 800 | 1550 | 3500 |
| IGROV | 110 | 50 | 3200 | 80 | 227 | 2400 |
| M19MEL | 400 | 250 | 1500 | 320 | 780 | 5500 |
| A498 | 200 | 110 | 1000 | 160 | 1200 | 18000 |
| H226 | 200 | 400 | 1300 | 350 | 3158 | 25000 |

The data clearly reflect the very high and often better cytotoxic activity of compounds of the formulae 8–11 than cis-platin of the formula 3 and carboplatin of the formula 4.

The mammalian toxicity [$LD_{50}$] of the compounds prepared by the process of the present invention were determined in Swiss Albino mice by peroval route using the staircase method followed by pubit scale analysis [M. N. Ghosh in "Fundamentals of Experimental Pharmacology", Scientific Book Agency, India, pp. 64–88 (1971)] and were found to be within the range of 630–962 mg/kg p.o. Under similar conditions the toxicity of cis-platin obtained was 31 mg/kg p.o. In other words, the pharmacy index of compounds of the formula 1 prepared by the process of the present invention are very high.

The details of the invention are given in the examples provided below which are given for illustrations only and should not be construed to limit the scope of the present invention.

EXAMPLE 1

A mixture of tin powder (35 g) and benzyl chloride (40 g) in toluene is refluxed for six hours and filtered hot. The filtrate was concentrated to obtain dibenzyltin dichloride (85%). To a clear hot solution of Dibenzyltin dichloride (5 gm.) in toluene (50 ml) is added a solution of indole (3.157 gm.). After stirring at ambient temperature for 3 hr. the precipitated crystals are filtered, washed three times with hexane (15 ml.) and finally dried in vacuo to obtain the bis(indole) complex of dibenzyltindichloride. It was further recrystallized from chloroform/petroleum ether to afford pure bis(indole) complex of dibenzyltindichloride (87%) of formula 8.

Analysis: Calcd. (% by weight): C, 59.61; H, 5.29; Cl, 11.74; Sn, 19.65. Found (% by weight): C, 59.33; H, 5.01; Cl, 11.25; Sn, 19.90.

EXAMPLE 2

To a solution of Dibenzyltin dichloride (5 gm.) in toluene (50 ml) is added a solution of thiophene (2.25 gm.). After stirring at 40° C. for 2 hr. and cooling the mixture to room temperature, the precipitated crystals are filtered, washed three times with hexane (35 ml.) and finally dried in vacuo to obtain the bis(thiophene) complex of dibenzyltindichloride. It was further recrystallized from chloroform/petroleum ether to afford pure bis(thiophene) complex of dibenzyltindichloride (95% ) of formula 8.

Analysis: Calcd. (% by weight): C, 48.89; H, 4.07; Cl, 13.13; Sn, 21.98. Found (% by weight): C, 49.01; H, 3.94; Cl, 13.32; Sn, 21.76.

EXAMPLE 3

To a clear hot solution of Dibenzyltin dichloride (5 gm.) in toluene (50 ml) is added a solution of imidazole (1.832 gm.). After stirring at 50° C. for 1 hr. and cooling the mixture to room temperature, the precipitated crystals are filtered, washed three times with hexane (35 ml.) and finally dried in vacuo to obtain the bis(imidazole) complex of dibenzyltindichloride. It was further recrystallized from chloroform/petroleum ether to afford pure bis(imidazole) complex of dibenzyltindichloride (90%) of formula 10.

Analysis: Calcd. (% by weight): C, 47.45; H, 4.34; Cl, 14.02; Sn, 23.46. Found (% by weight): C, 47.44; H, 4.12; Cl, 14.51; Sn, 23.77.

EXAMPLE 4

To a clear hot solution of Dibenzyltin dichloride (5 gm.) in toluene (50 ml) is added a solution of bipyridine (2.101 gm.). After stirring at ambient temperature for 3 hr. the precipitated crystals are filtered, washed three times with hexane (15 ml.) and finally dried in vacuo to obtain the bipyridine complex of dibenzyltindichloride. It was further recrystallized from chloroform/petroleum ether to afford pure bipyridine complex of dibenzyltindichloride (78%) of formula 11.

Analysis: Calcd. (% by weight): C, 54.56; H, 4.16; Cl, 13.43; Sn, 22.48. Found (% by weight): C, 54.11; H, 4.02; Cl, 13.68; Sn, 22.10.

EXAMPLE 5

To a clear solution of Dibenzyltin dichloride (3 g.) in 100 ml of methanol was added potassium thiocyanate (2.1 g.) and the mixture was stirred for 12 hr. After filtration and filtrate was concentrated to yield dibenzyltin diisothiocyanate as a white crystalline solid. To a clear solution of Dibenzyltin diisothiocyanate (2 gm.) in methanol (50 ml) is added a solution of phenanthroline (1.038 gm.). After stirring at ambient temperature for 2 hr. the precipitated crystals are filtered, washed three times with hexane (25 ml.) and finally dried in vacuo to obtain the phenanthroline complex of dibenzyltin diisothiocyanate. It was further recrystallized from chloroform/petroleum ether to afford pure phenanthroline complex of dibenzyltin diisothiocyanate (80%) of formula 1 where x=thiocyanate.

Analysis: Calcd. (% by weight): C, 58.13; H, 5.54; N 7.24; Sn, 19.32 Found (% by weight): C, 58.02; H, 5.23; N 6.98; Sn, 19.68.

We claim:

1. A compound as of the formula:

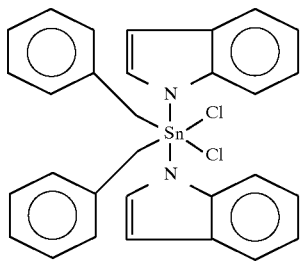

2. A compound of the formula:

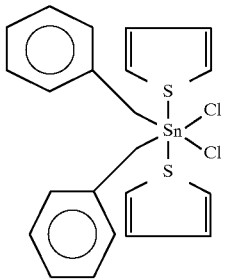

3. A compound of the formula:

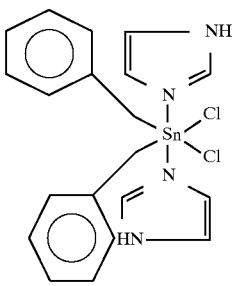

4. A compound of the formula:

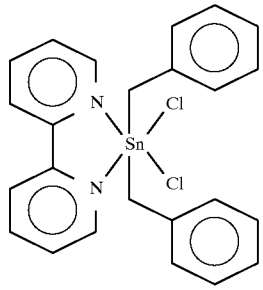

* * * * *